US011123084B2

(12) United States Patent
Weiss et al.

(10) Patent No.: US 11,123,084 B2
(45) Date of Patent: Sep. 21, 2021

(54) SURGICAL INSTRUMENTARIUM

(71) Applicant: Aesculap AG, Tuttlingen (DE)

(72) Inventors: Josef-Benedikt Weiss, Rottweil (DE); Michael Utz, Tuttlingen (DE); Martin Nonnenmann, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 16/194,724

(22) Filed: Nov. 19, 2018

(65) Prior Publication Data

US 2019/0150947 A1  May 23, 2019

(30) Foreign Application Priority Data

Nov. 23, 2017  (DE) ............. 10 2017 127 737.4

(51) Int. Cl.
*A61B 17/15* (2006.01)
*A61B 17/14* (2006.01)
*A61B 17/17* (2006.01)

(52) U.S. Cl.
CPC .......... *A61B 17/155* (2013.01); *A61B 17/142* (2016.11); *A61B 17/157* (2013.01); *A61B 17/17* (2013.01)

(58) Field of Classification Search
CPC ... A61B 17/154; A61B 17/155; A61B 17/157; A61B 17/1764
See application file for complete search history.

(56) References Cited

U.S. PATENT DOCUMENTS

| | | | |
|---|---|---|---|
| 5,474,559 A | 12/1995 | Bertin et al. | |
| 5,709,689 A | 1/1998 | Ferrante et al. | |
| 6,852,115 B2 * | 2/2005 | Kinnett | A61B 17/15 606/88 |
| 7,621,919 B2 | 11/2009 | Williams, III et al. | |
| 7,704,253 B2 | 4/2010 | Bastian et al. | |
| 8,016,833 B2 | 9/2011 | Roger et al. | |
| 8,573,101 B2 | 11/2013 | Thomaschewski | |
| 8,591,516 B2 | 11/2013 | Metzger et al. | |
| 8,808,298 B2 | 8/2014 | Raub et al. | |

(Continued)

FOREIGN PATENT DOCUMENTS

| | | |
|---|---|---|
| EP | 1900465 | 3/2008 |
| EP | 2228023 | 9/2010 |

(Continued)

*Primary Examiner* — Matthew J Lawson
*Assistant Examiner* — Lisa Nguyen
(74) *Attorney, Agent, or Firm* — Lipsitz & McAllister, LLC

(57) ABSTRACT

In order to improve a surgical instrumentarium for preparing a femur and a tibia for the implantation of the knee joint endoprosthesis, which instrumentarium comprises a first sawing template with three guidance slots for guiding a saw blade, which three guidance slots define three intersecting cutting planes, in such a way that the number of necessary instruments of the instrumentarium may be reduced, it is proposed that the instrumentarium comprises a second sawing template, that the second sawing template has a fourth guidance slot for guiding a saw blade, and that the first sawing template and the second sawing template are coupled to each other in a force- and/or form-fitting manner in a coupling position and are separated from each other in a separating position.

23 Claims, 13 Drawing Sheets

(56) References Cited

U.S. PATENT DOCUMENTS

Figure 1:
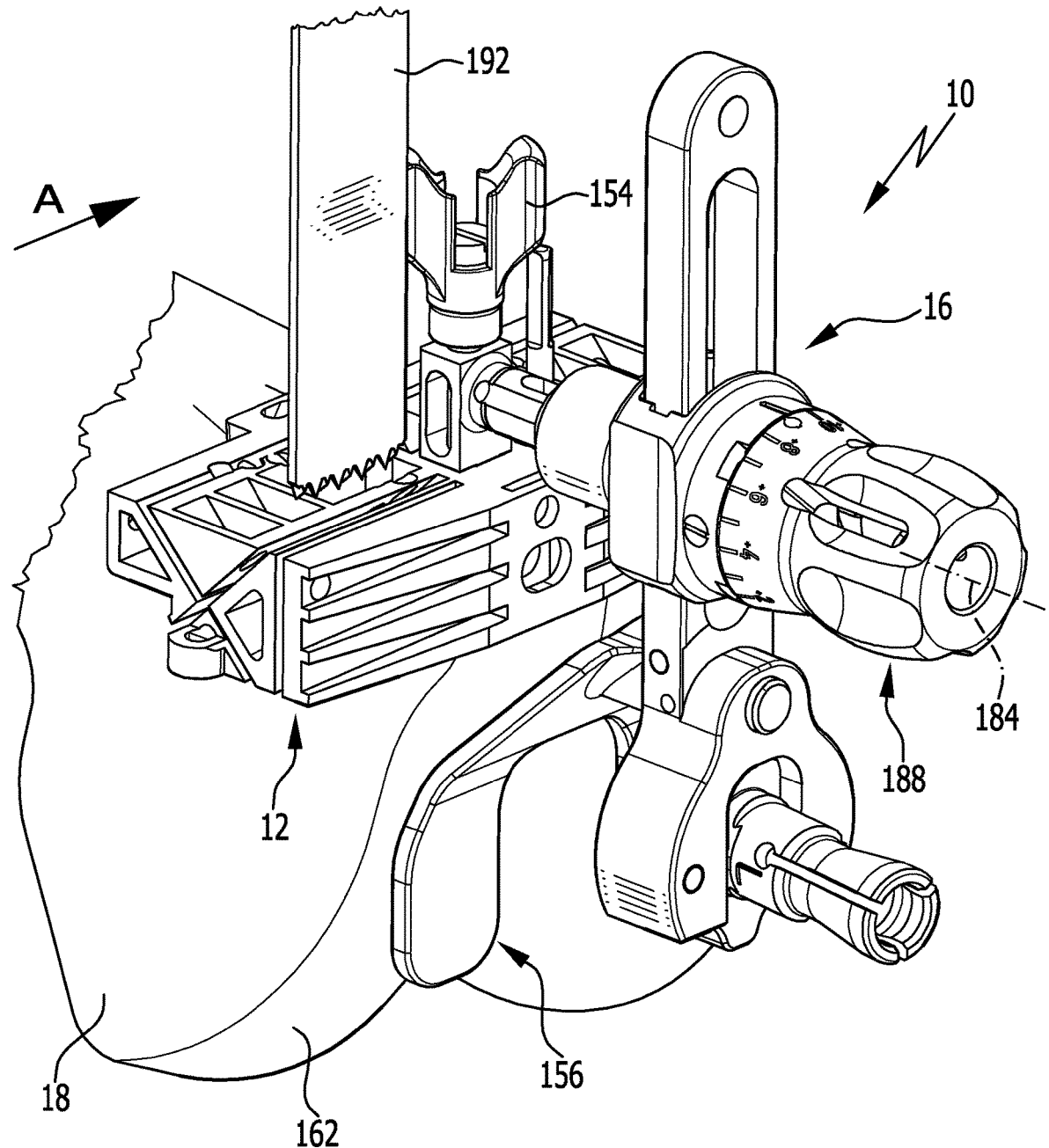

| | | | |
|---|---|---|---|
| 8,844,418 B2 | 9/2014 | Thomaschewski | |
| 2001/0001121 A1* | 5/2001 | Lombardo | A61B 17/1668 606/89 |
| 2007/0073305 A1* | 3/2007 | Lionberger | A61B 17/155 606/87 |
| 2007/0173849 A1* | 7/2007 | Claypool | A61B 17/155 606/87 |
| 2008/0066602 A1 | 3/2008 | Thomaschewski | |
| 2011/0172672 A1 | 7/2011 | Dubeau et al. | |
| 2012/0031246 A1 | 2/2012 | Thomaschewski | |
| 2012/0310246 A1 | 12/2012 | Belcher et al. | |
| 2013/0296865 A1 | 11/2013 | Aram et al. | |
| 2013/0317510 A1 | 11/2013 | Couture et al. | |
| 2013/0325017 A1 | 12/2013 | Lomicka | |
| 2014/0257307 A1* | 9/2014 | Johannaber | A61B 17/17 606/88 |
| 2015/0238201 A1 | 8/2015 | Carroll et al. | |

FOREIGN PATENT DOCUMENTS

| | | |
|---|---|---|
| EP | 2623044 | 8/2013 |
| EP | 2626044 | 9/2013 |
| EP | 2668916 | 12/2013 |
| EP | 2679173 | 1/2014 |
| EP | 2445419 | 2/2014 |
| WO | 9729697 | 8/1997 |
| WO | 9965403 | 12/1999 |
| WO | 2013078076 | 5/2013 |

* cited by examiner

SURGICAL INSTRUMENTARIUM

CROSS-REFERENCE TO RELATED APPLICATIONS

The present disclosure claims the benefit of German application number 10 2017 127 737.4 of Nov. 23, 2017, which is incorporated herein by reference in its entirety and for all purposes.

FIELD OF THE INVENTION

The present invention relates to surgical instrumentaria generally, and more specifically to a surgical instrumentarium for preparing a femur and a tibia for the implantation of a knee joint endoprosthesis, which instrumentarium comprises a first sawing template with three guidance slots for guiding a saw blade, which three guidance slots define three intersecting cutting planes.

BACKGROUND OF THE INVENTION

Surgical instrumentaria of the kind described at the outset are known, e.g., from U.S. Pat. No. 5,709,689. Disclosed in said document is a sawing template with three slots for preparing a femur before the implantation of a femoral component of a knee joint endoprosthesis.

A problem in instrumentaria of that kind is in particular that different sawing templates are used for preparing the femur and the tibia. The number of sawing templates may further increase if different sawing templates are used for left and right knee joint endoprostheses. Typically five saw cuts need to be placed on the femur. On the tibia, however, only one cut is provided in order to prepare a planar tibial face facing in the direction toward the femur.

The production of the sawing templates is cumbersome and associated with high costs.

SUMMARY OF THE INVENTION

In a first aspect of the invention, a surgical instrumentarium for preparing a femur and a tibia for the implantation of a knee joint endoprosthesis comprises a first sawing template with three guidance slots for guiding a saw blade. The three guidance slots define three intersecting cutting planes. The instrumentarium comprises a second sawing template. The second sawing template has a fourth guidance slot for guiding a saw blade. The first sawing template and the second sawing template are coupled to each other in at least one of a force- and form-fitting manner in a coupling position and are separated from each other in a separating position. The three cutting planes intersect in three intersection lines and the three intersection lines run parallel to each other.

In a second aspect of the invention, a surgical instrumentarium for preparing a femur and a tibia for the implantation of a knee joint endoprosthesis comprises a first sawing template with three guidance slots for guiding a saw blade. The three guidance slots define three intersecting cutting planes. The instrumentarium comprises a second sawing template. The second sawing template has a fourth guidance slot for guiding a saw blade. The first sawing template and the second sawing template are coupled to each other in at least one of a force- and form-fitting manner in a coupling position and are separated from each other in a separating position. The three cutting planes intersect in three intersection lines. The three intersection lines run parallel to each other. The instrumentarium comprises an alignment instrument and the alignment instrument and the first sawing template are connected to each other in at least one of a force- and form-fitting manner in an alignment position and are separated from each other in a storing position.

BRIEF DESCRIPTION OF THE DRAWING FIGURES

Figure 2:
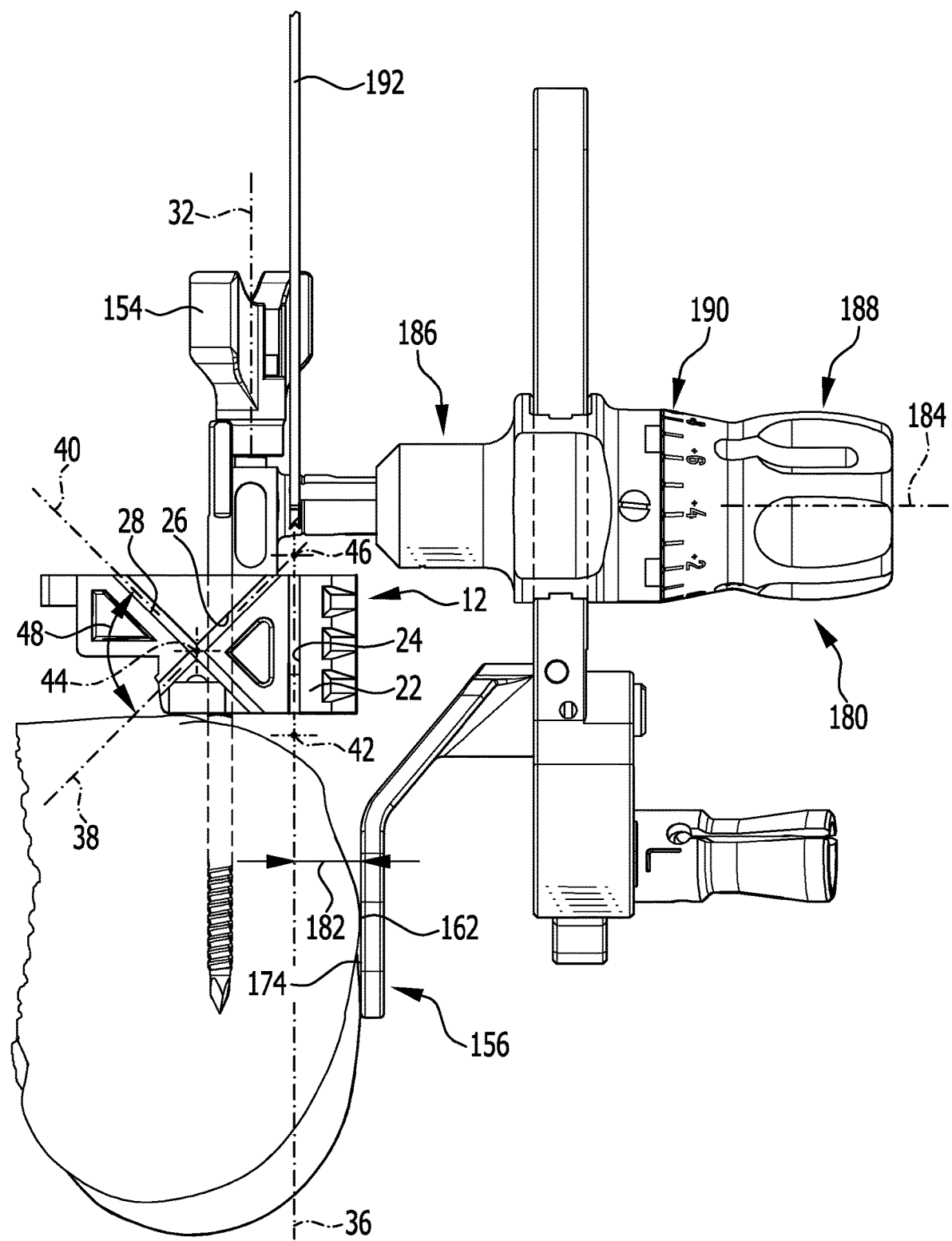
Figure 3:
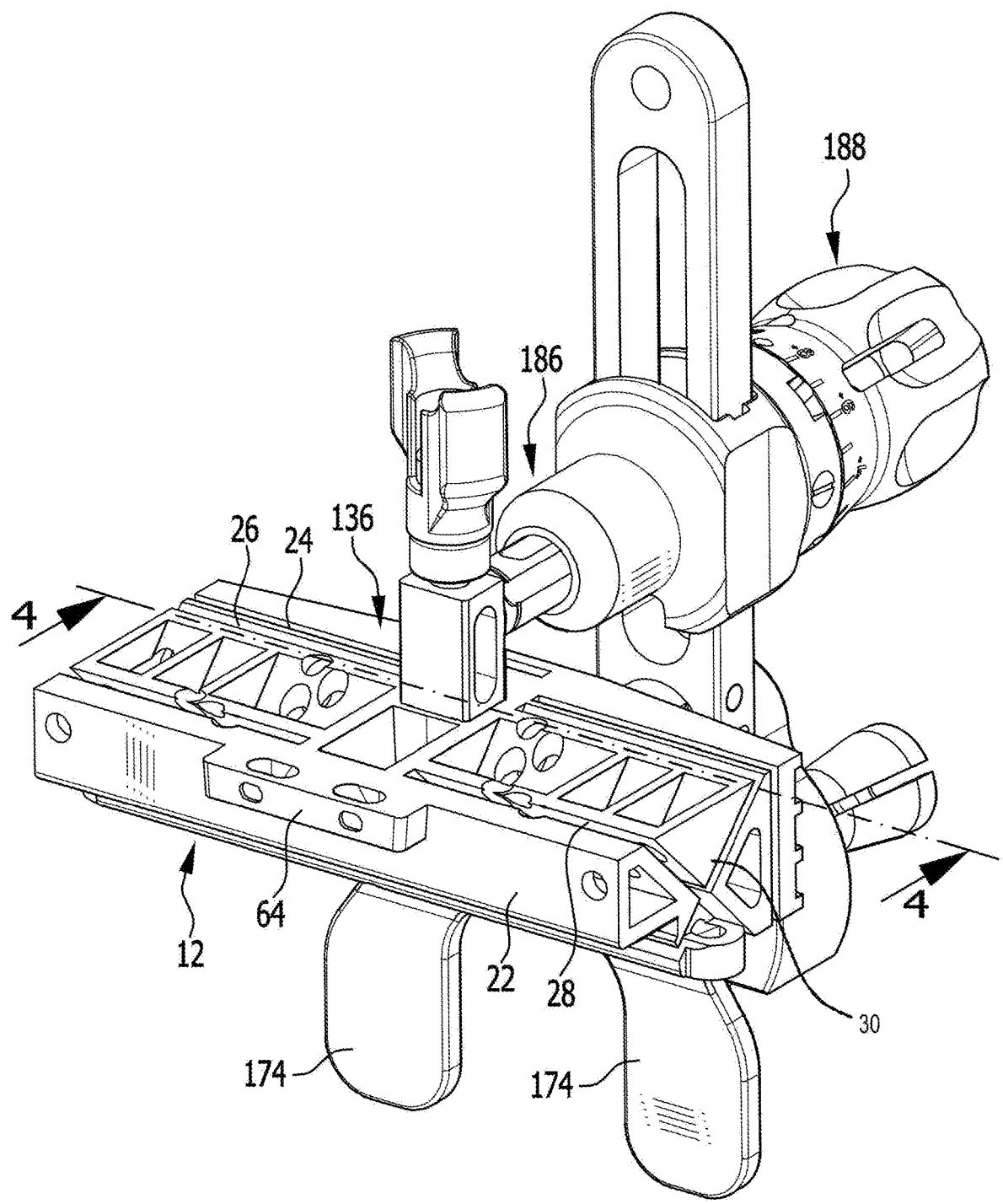
Figure 4:
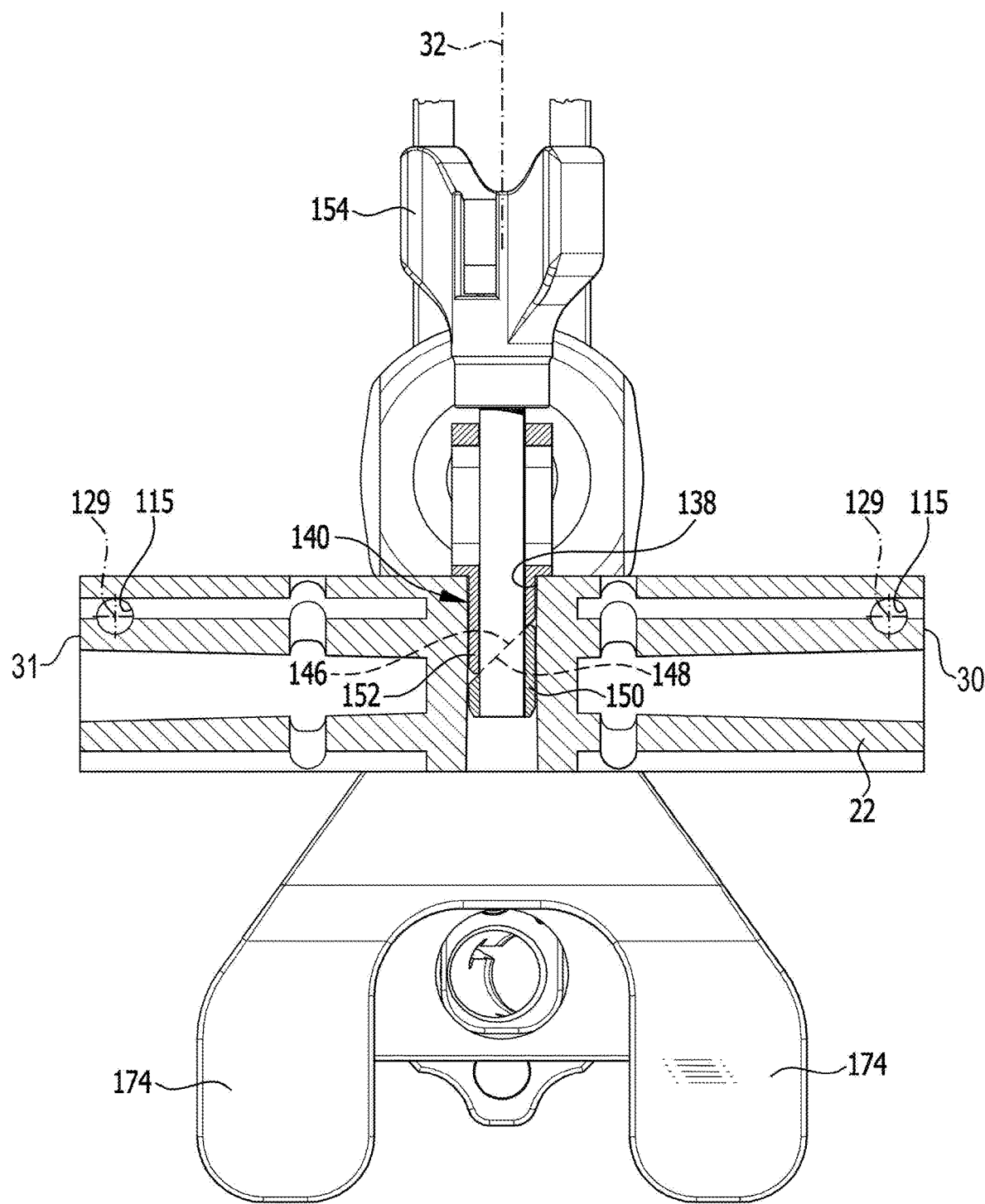
Figure 5A:
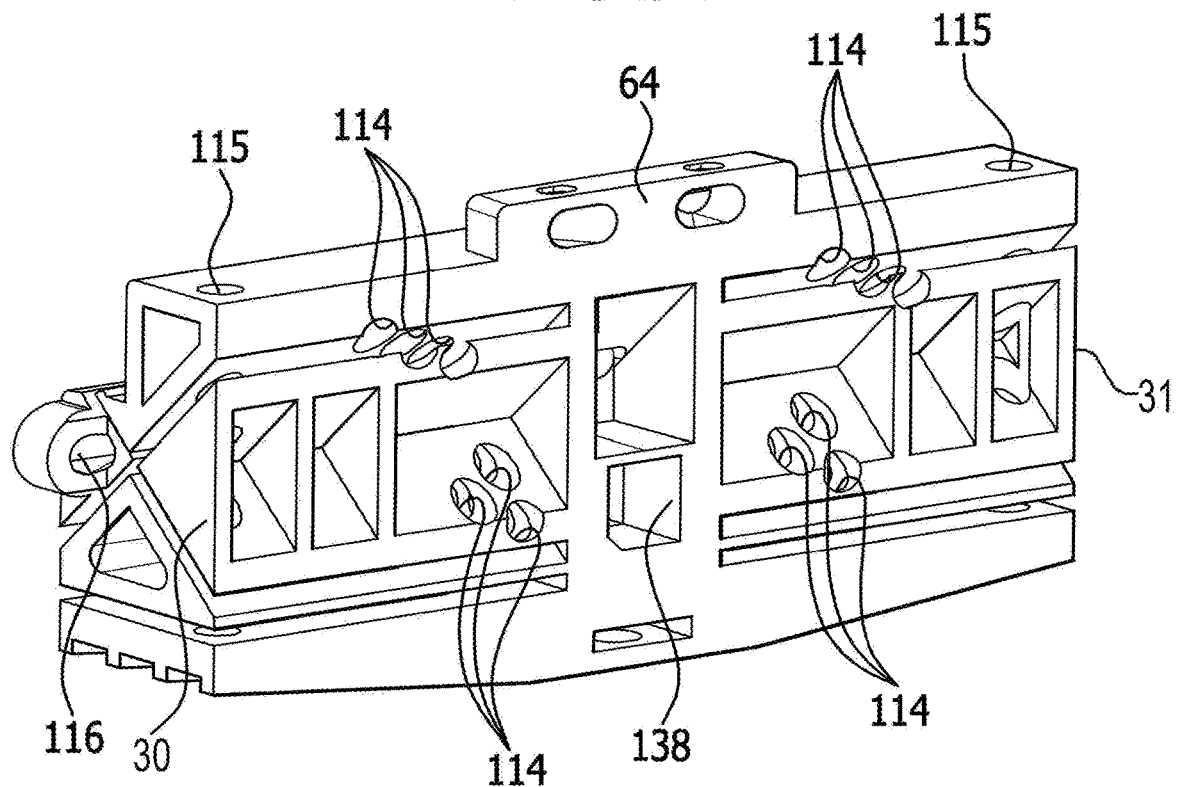
Figure 5B:
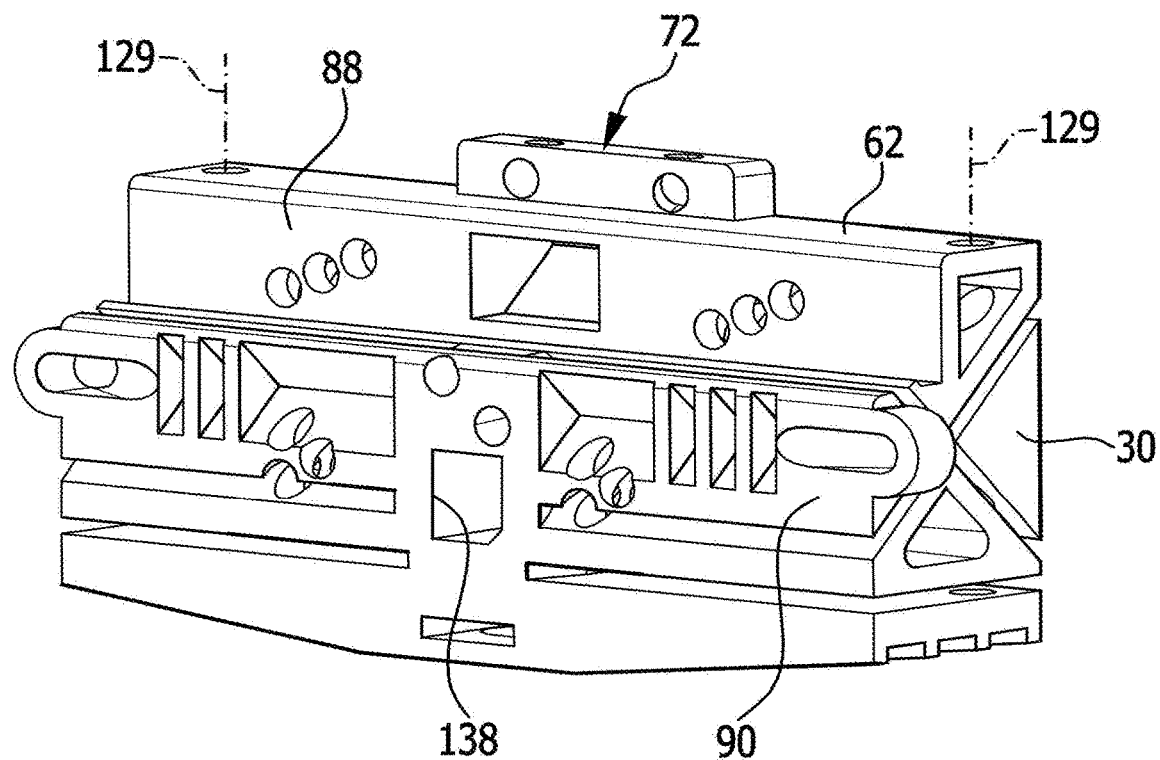
Figure 6:
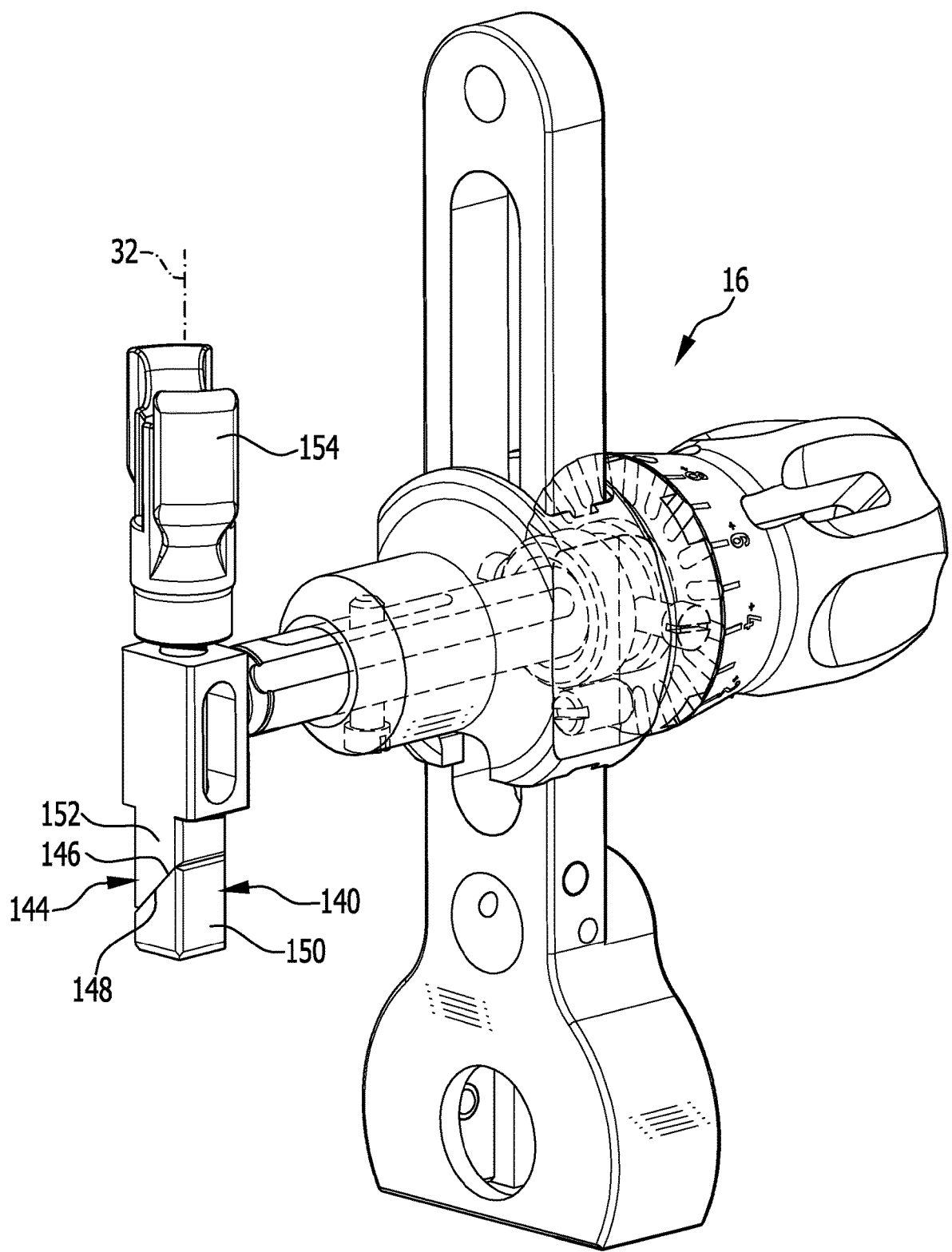
Figure 7:
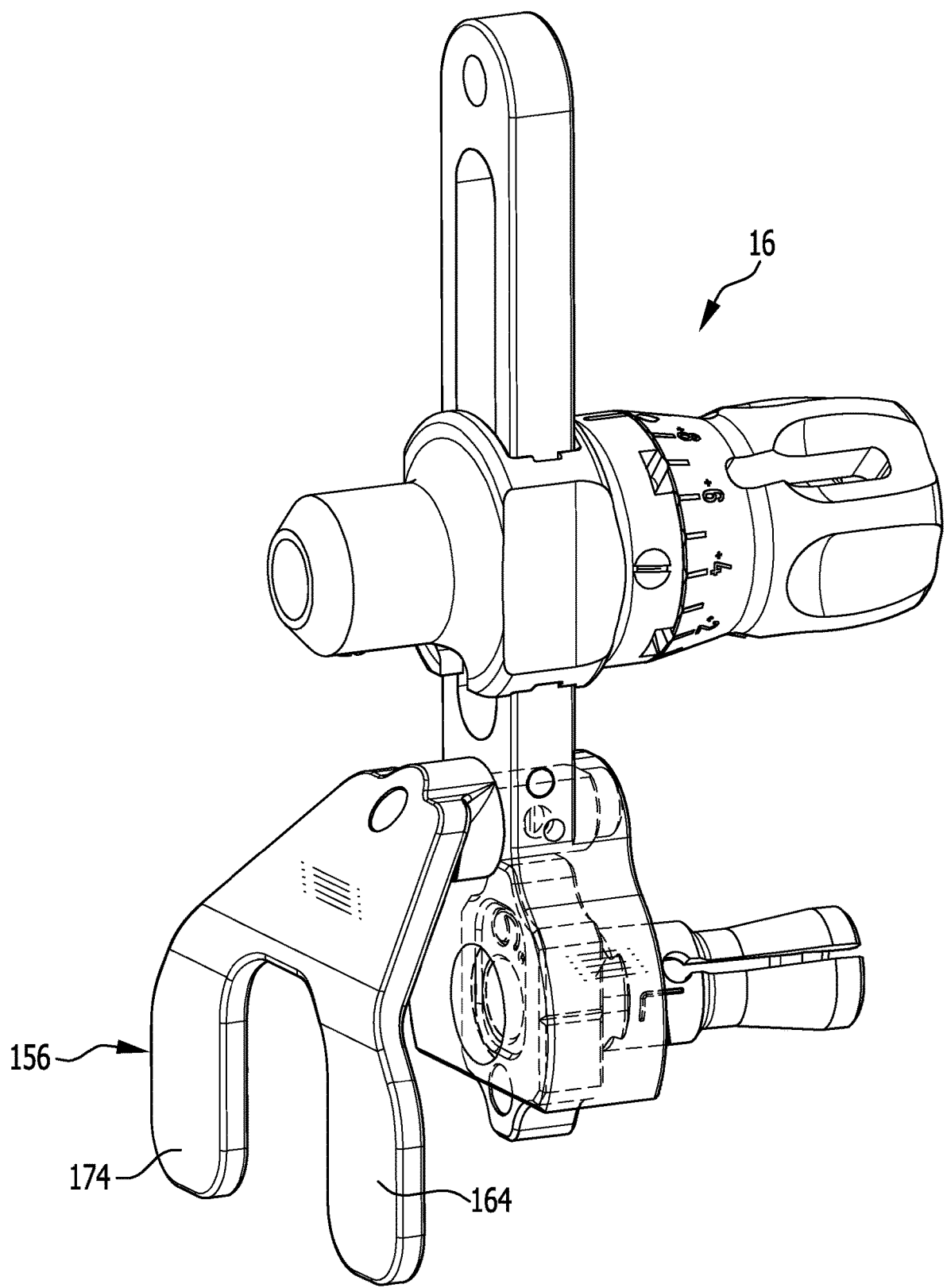
Figure 8:
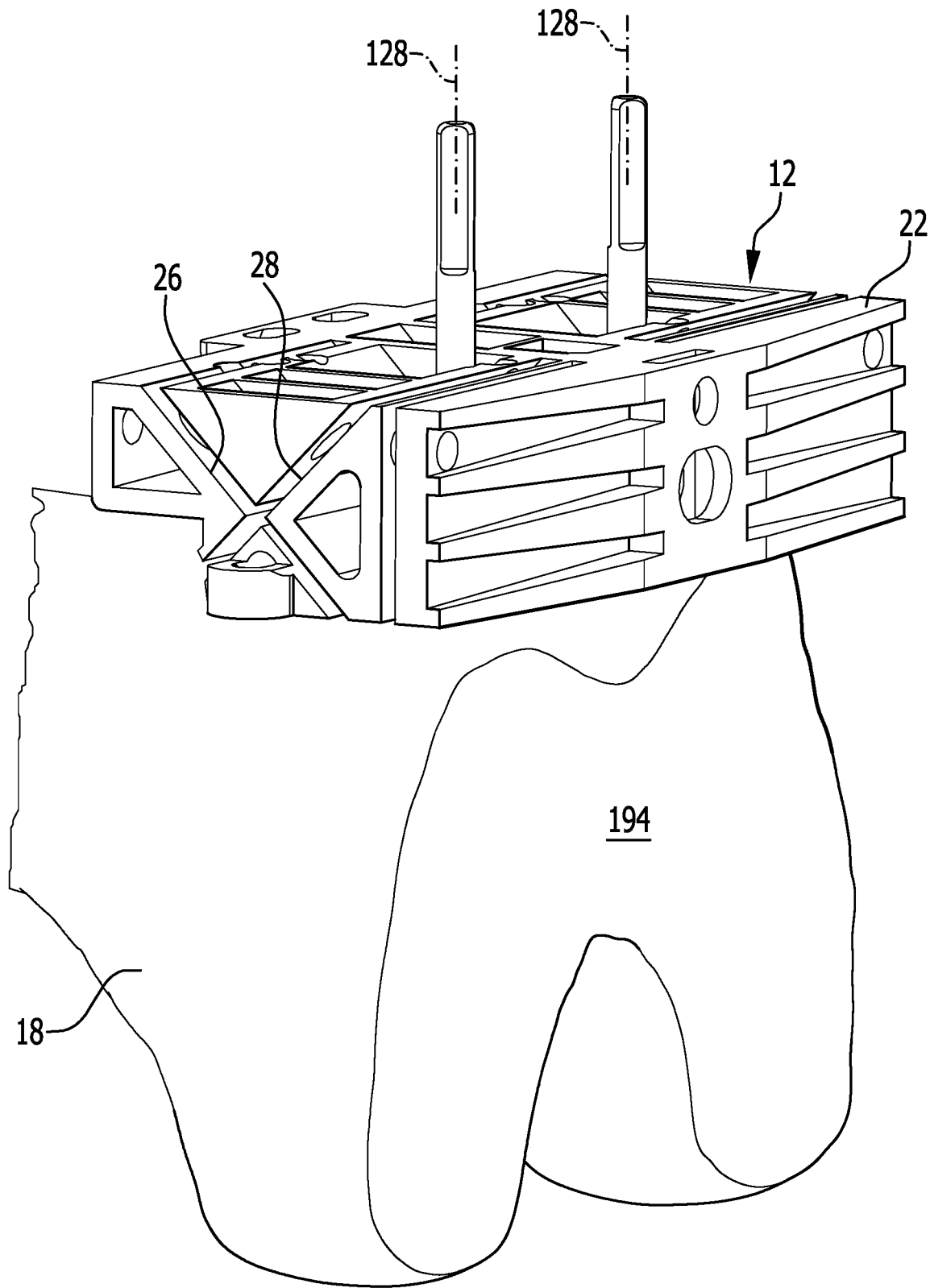
Figure 9:
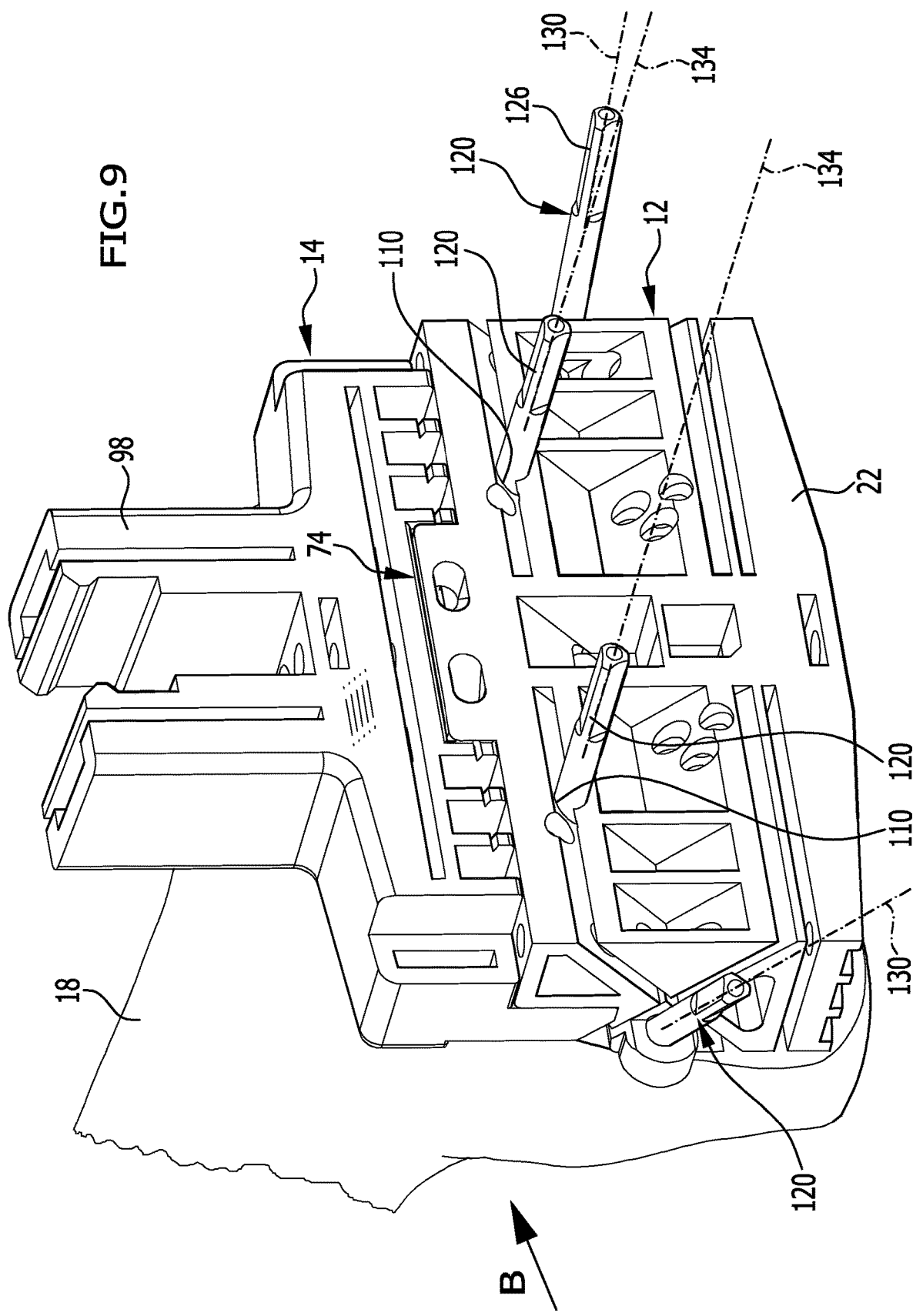
Figure 10:
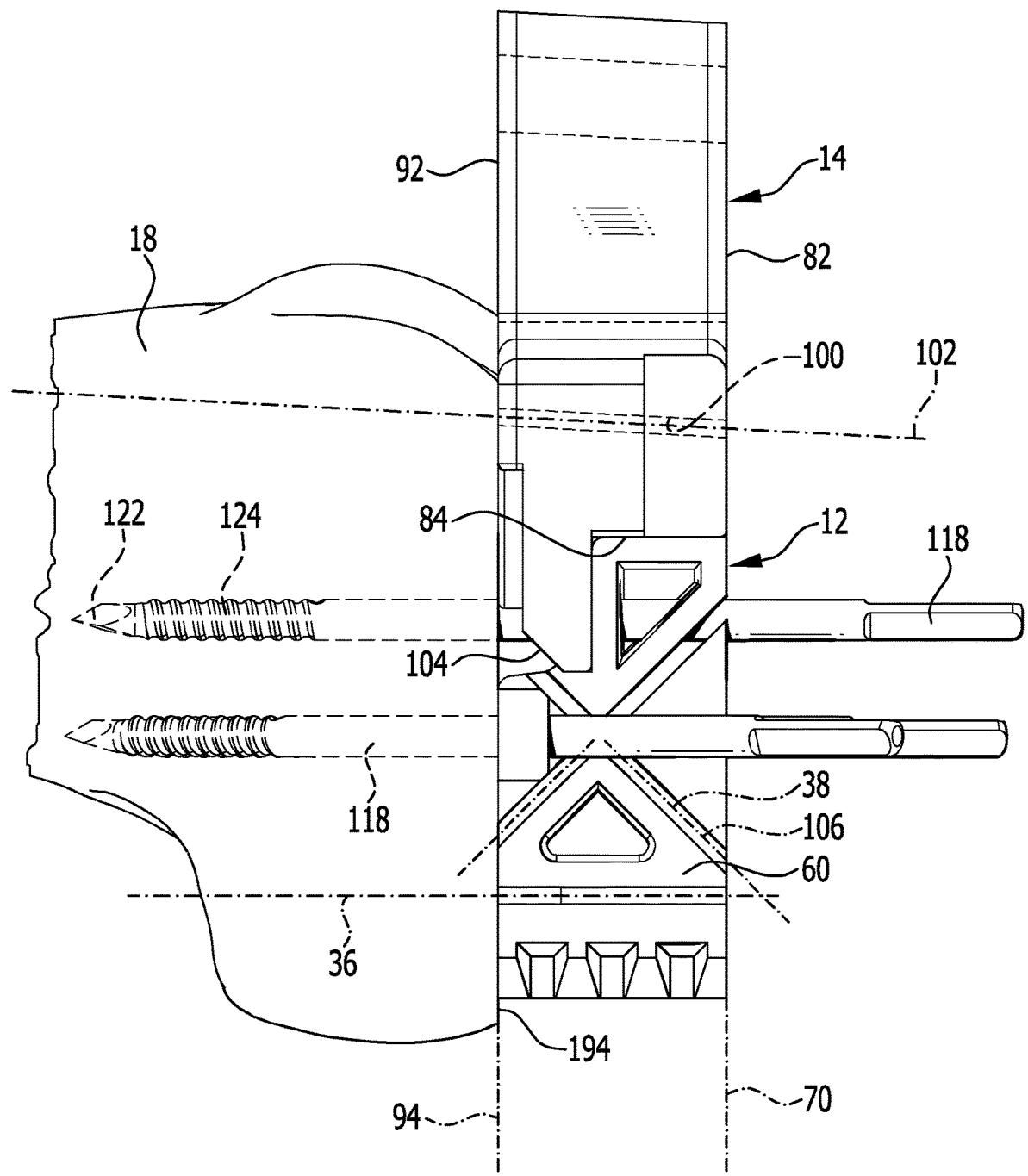
Figure 11:
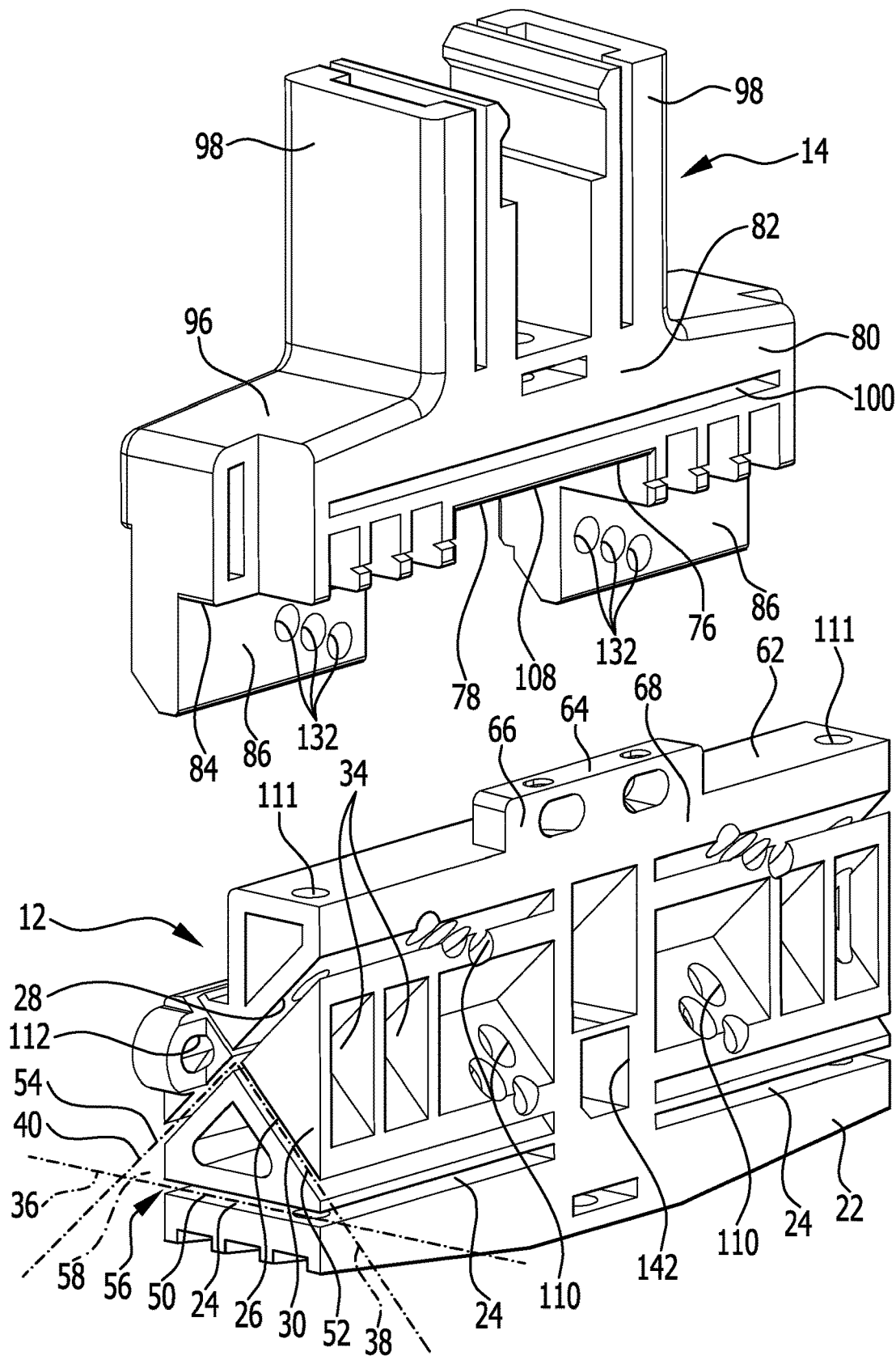
Figure 12:
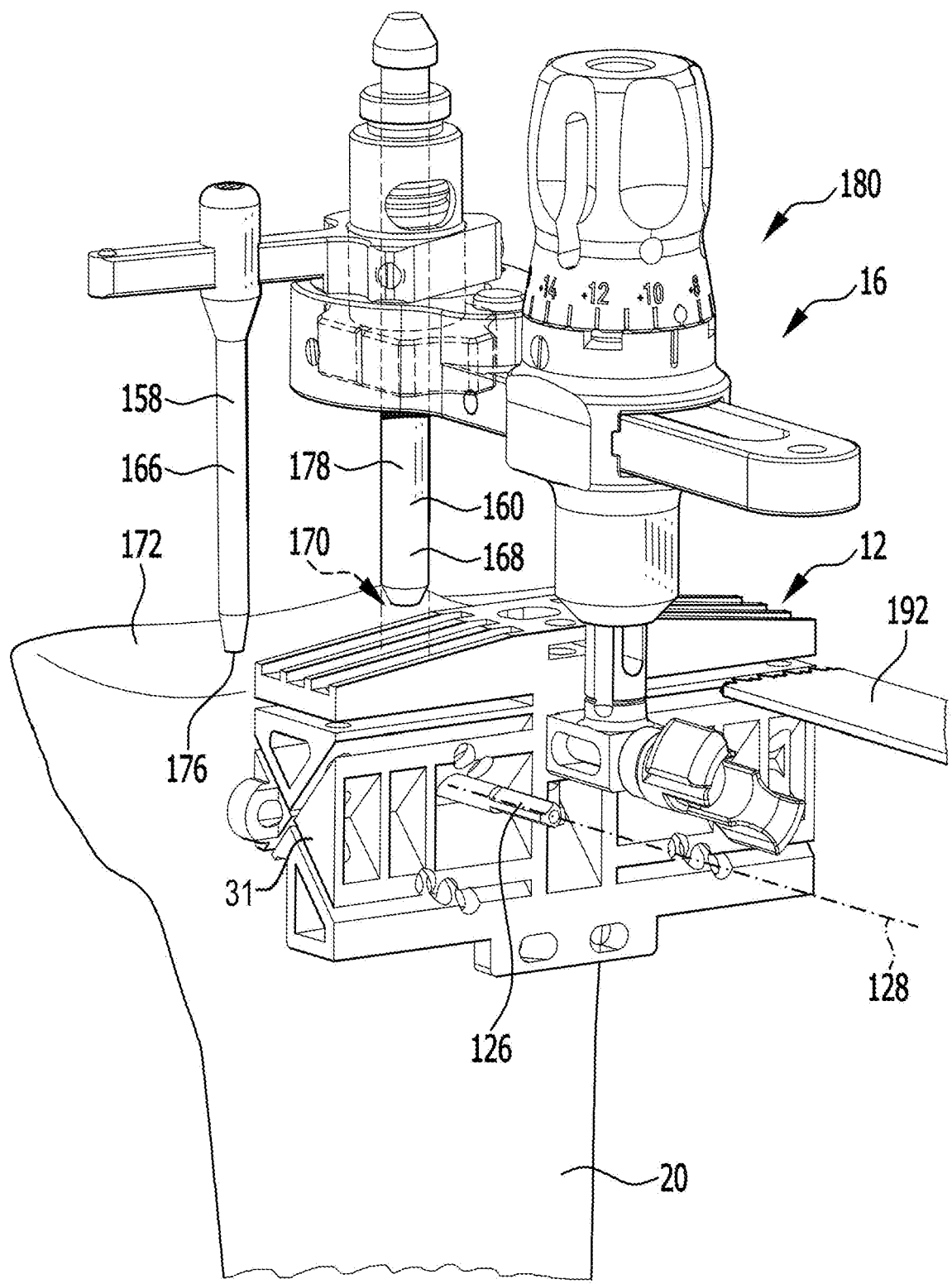
Figure 13:
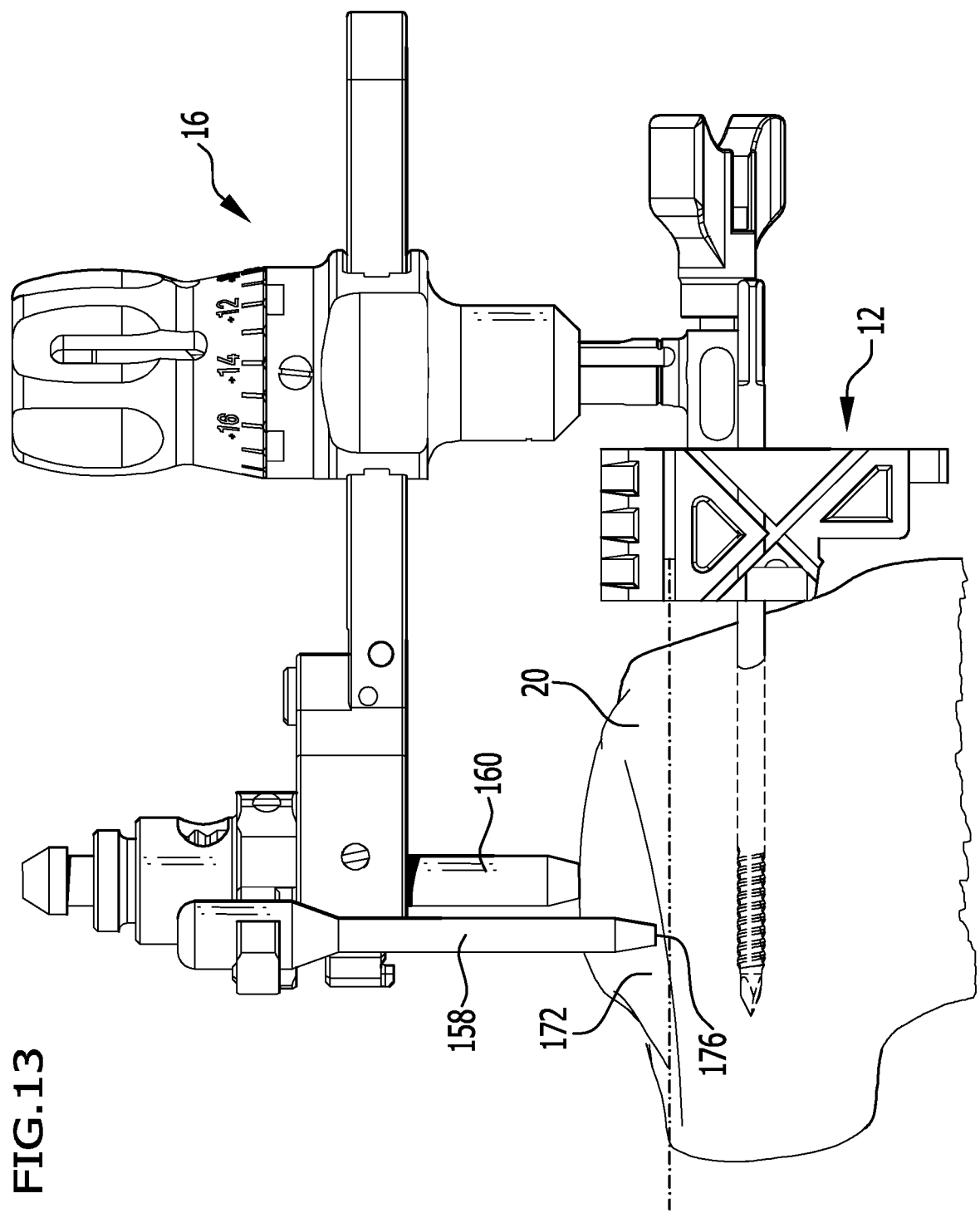

The foregoing summary and the following description may be better understood in conjunction with the drawing figures, of which:

FIG. 1: shows a perspective total view of an alignment instrument of a medical instrumentarium with first sawing template coupled thereon upon placing the distal cut on the femur;

FIG. 2: shows a side view in the direction of arrow A;

FIG. 3: shows a further perspective view of the arrangement from FIGS. 1 and 2 without a bone and without a saw blade;

FIG. 4: shows a sectional view along line 4-4 in FIG. 3;

FIG. 5A: shows a perspective view of the first sawing template from the front;

FIG. 5B: shows a perspective view of the first sawing template from the back;

FIG. 6: shows a perspective view of an alignment instrument with a second connecting element;

FIG. 7: shows a perspective view of the alignment instrument with an abutment body for abutting against a femur;

FIG. 8: shows a perspective view of the first sawing template fixed on the femur after preparation of the distal femoral cut;

distal femur cut with a second sawing template coupled thereon with a total of four fixing pins;

FIG. 10: shows a partially broken side view in the direction of arrow B in FIG. 9;

FIG. 11: shows a perspective exploded depiction of the first sawing template and the second sawing template in a separating position;

FIG. 12: shows a perspective total view of the alignment instrument with alternative abutment bodies and a first sawing template connected on the alignment instrument on the tibia; and FIG. 13: shows a further perspective view of the arrangement from FIG. 12.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical instrumentarium for preparing a femur and a tibia for the implantation of a knee joint endoprosthesis, which instrumentarium comprises a first sawing template with three guidance slots for guiding a saw blade, which three guidance slots define three intersecting cutting planes, wherein the instrumentarium comprises a second sawing template, wherein the second sawing template has a fourth guidance slot for guiding a saw blade, wherein the first sawing template and the second sawing template are coupled to each other in at least one of a force- and form-fitting manner in a coupling position and are separated from each other in a separating position, wherein the three cutting planes intersect in three intersection lines and wherein the three intersection lines run parallel to each other.

The further development proposed in accordance with the invention of a surgical instrumentarium of the kind described at the outset enables in particular performing all cuts on the femur and tibia with only the two sawing templates. For that purpose, in particular a first cut, the so-called distal cut, may be performed on the femur in order to prepare a planar bone face facing in the direction toward the tibia in an extended position of the leg. In a second step, the two sawing blocks may then be fixed, coupled to each other at the coupling position, on the prepared planar femoral face. Then the four further cuts may be performed on the femur. The two sawing templates thus form in the coupling position a so-called 4-in-1 sawing block. Further, the first sawing template may be used in order to perform the tibial cut. For this purpose, the first sawing template is fixed on the tibia in a desired manner. For guiding a saw blade, in particular the same guidance slot may be used as for the distal cut on the femur. The further developed instrumentarium thus enables managing with only two sawing templates for preparing both a femur and a tibia. In this way, the number of required elements of the instrumentarium may be reduced and thus also the costs for the production, cleaning, and sterilization thereof. For a surgeon, an instrumentarium reduced in that way has the advantage that a risk of mistaking individual instruments and sawing templates of the instrumentarium is significantly minimized. This may be achieved in particular in that the two sawing templates significantly differ in their shape. Coupling the first sawing template and the second sawing template to each other in the coupling position additionally has the advantage that only one of the two sawing templates must be arranged on the femur for the positioning. The second sawing template may then be coupled to the sawing template already arranged or fixed on the femur. If it is not needed, it may be removed. This improves a view of the surgical site.

It is favorable if the instrumentarium comprises a coupling device with at least one first coupling element and at least one second coupling element, if the at least one first coupling element is arranged or formed on the first sawing template, if the at least one second coupling element is arranged or formed on the second sawing template, and if the at least one first coupling element and the at least one second coupling element are in engagement in the coupling position and are disengaged in the separating position. Providing a coupling device of that kind enables coupling the first sawing template and the second sawing template to each other in a simple and defined manner, in order to form a 4-in-1 sawing template in the coupling position. The coupling elements in engagement with each other may be in engagement in a force- and/or form-fitting manner.

It is advantageous if the at least one first coupling element is configured in the form of a coupling projection or a coupling recess and if the at least one second coupling element is formed corresponding to the at least one first coupling element. In particular, the second coupling element may be configured in the form of a coupling recess or a coupling projection, depending on whether the first coupling element is configured in the form of a coupling projection or in the form of a coupling recess. A design of the coupling elements of that kind enables in a simple manner a force- and/or form-fit coupling of the two sawing templates to each other in the coupling position. For example, the coupling projection may be of two-part configuration with two parts moveable relative to each other, which in an insertion position define a minimum cross section and in a clamping position, when they are inserted into a coupling recess, define a maximum cross section in order to hold the two coupling elements in engagement in a clamping manner. Alternatively, the coupling elements may also be configured to form a latching or snapping connecting device, in particular in the form of latching or snapping elements able to be brought into engagement with each other.

The instrumentarium may be formed in a particularly simple manner if the coupling recess is configured in the form of at least one set-back portion on the first or second sawing template. Such a set-back portion may in particular define a cuboidal coupling recess which is not entirely closed all the way around, but instead of five, for example, provides only four side faces for delimiting the coupling recess.

The first sawing template favorably comprises a first base body on which the three guidance slots are formed. The production of the first sawing template is thus particularly simple because the guidance slots may be incorporated into the base body, for example by machining the base body. Alternatively, it is also conceivable to form the sawing templates from a metal or a plastic through a shaping process. For example, the first sawing template, this applies analogously to the second sawing template, may be produced by a manufacturing method, for example by 3D-printing, selective laser sintering, or an injection molding method.

It is further favorable if the second sawing template comprises a second base body on which the fourth guidance slot is formed. Similar to the first base body, the second base body may also be used as a solid material and be processed in such a way that a fourth guidance slot is formed. The selection of the materials and the production methods, too, may be provided for the second sawing template as with the first sawing template.

In order to be able to fix the first sawing template on a bone, it is advantageous if the first sawing template has at least one first fixing element receptacle for at least one first fixing element for optionally fixing the first sawing template on the femur or on the tibia. In particular, two, three, four, or even more fixing element receptacles may be provided. These may be configured in particular in the form of through-holes in order to fix the sawing template with bone screws or bone pins on the bone to be prepared.

It is favorable if the second sawing template has at least one second fixing element receptacle for at least one second fixing element for fixing the second sawing template on the femur. In particular, two, three, four or more fixing element receptacles may be provided on the second sawing template. The at least one second fixing element receptacle enables in particular also fixing the second sawing template itself on the bone to be processed, namely the femur.

It is further advantageous if the at least one first fixing element receptacle defines a first fixing element longitudinal axis, if the at least one second fixing element receptacle defines a second fixing element longitudinal axis, and if the at least one first fixing element longitudinal axis and the at least one second fixing element longitudinal axis coincide in the coupling position. This design enables in particular guiding one single fixing element through the at least one first and through the at least one second fixing element receptacle in order to fix the sawing templates coupled to each other in the coupling position together on the bone. In this way, it is possible in particular to attach both sawing templates to the bone in a defined manner with only two fixing elements.

Advantageously, at least one first fixing element receptacle is arranged or formed projecting over the first base body. This enables in particular guiding a fixing element through one or more first fixing element receptacles without having to pass through the second sawing template. This allows in particular fixing the first sawing template on the femur and then coupling the second sawing template to the first sawing template fixed on the femur. In this way, the second sawing template may again be removed from the first sawing template if the saw cut guided by the fourth guidance slot is performed on the femur.

It is favorable if at least two first fixing element receptacles are provided and if the first fixing element longitudinal axes thereof are aligned parallel or substantially parallel or inclined relative to each other. In particular with fixing element longitudinal axes inclined relative to each other, two first fixing element receptacles enable fixing the first sawing template selectively both on the femur and on the tibia with only two fixing elements in a defined and secure manner.

It is further advantageous if at least two second fixing element receptacles are provided and if the second fixing element longitudinal axes thereof are aligned parallel or substantially parallel or inclined relative to each other. With two second fixing element receptacles, the second sawing template may be fixed on the femur in a defined manner. In particular, the second fixing element longitudinal axes of the two second fixing element receptacles may be aligned with first fixing element longitudinal axes of two first fixing element receptacles of the first sawing template.

For forming a 4-in-1 sawing block, it is favorable if the fourth guidance slot in the coupling position runs parallel or substantially parallel to one of the three guidance slots of the first sawing template. In this way, two parallel bone faces may be prepared on the femur.

It is further favorable if the second sawing template has a guidance face, if the guidance face defines a guidance plane, and if the guidance plane in the coupling position is defined by one of the three cutting planes. In other words, the guidance face of the second sawing template may lengthen one of the three guidance slots on the first sawing template and thus define an improved guidance for a saw blade. For example, the guidance face may be formed by an outer face on the second base body.

It is advantageous if the fourth guidance slot defines a fourth cutting plane and if the fourth cutting plane in the coupling position runs parallel or substantially parallel to one of the three cutting planes of the first sawing template. This design enables in particular preparing on the femur two parallel or substantially parallel bone faces. This is favorable in particular if the femoral component of the knee joint endoprosthesis has two parallel bone contact surfaces.

In accordance with a further preferred embodiment of the invention, provision may be made for the three cutting planes to intersect in three intersection lines and for the three intersection lines to run parallel to each other. In this way, bone faces on the femur may be prepared such that the femoral component may be brought up to the prepared femur in particular parallel to the intersection lines.

The first sawing template may be formed in a particularly simple manner if two of the three cutting planes intersect at a right angle or substantially at a right angle. This enables in particular preparing two bone faces on the femur running at a right angle or substantially at a right angle to each other.

It is advantageous if the three cutting planes of the first sawing template define jacket surfaces of a straight prism which has a base surface in the form of a triangle, in particular in the form of an isosceles or equilateral or right triangle. If the three cutting planes are aligned in that way, then the three intersection lines defined by the three pairwise intersecting cutting planes likewise run parallel to each other. Such a first sawing template may be produced in a simple manner. In addition, the saw cuts to be carried out on the femur may be performed in a simple manner with said sawing template.

It is advantageous if the instrumentarium comprises an alignment instrument and if the alignment instrument and the first sawing template are connected to each other in a force- and/or form-fitting manner in an alignment position and are separated from each other in a storage position. With the alignment instrument, the first sawing template may be positioned on the femur or on the tibia in a desired manner, for example navigation-supported with the use of a medical navigation system. For this purpose, the alignment instrument may be brought up to one of the two bones in a defined manner and the first sawing template may be appropriately positioned when it is connected to the alignment instrument.

The alignment instrument and the first sawing template may be connected to each other in a simple manner if the instrumentarium comprises a connecting device with at least one first connecting element and at least one second connecting element, if the at least one first connecting element is arranged or formed on the first sawing template, if the at least one second connecting element is arranged or formed on the alignment instrument, and if the at least one first connecting element and the at least one second connecting element are in engagement in the alignment position and are disengaged in the storing position.

The first sawing template and the alignment instrument may be connected to each other in a simple manner if the at least one first connecting element is configured in the form of a connecting projection or a connecting recess and if the at least one second connecting element is formed corresponding to the at least one first connecting element. In particular, the at least one second connecting element may be configured in the form of a connecting recess or a connecting projection. Further, it is possible to configure the first and second connecting elements in a manner as is described in connection with the first and second coupling elements for coupling the first sawing template and the second sawing template. In particular, the first and second connecting elements may be configured in the form of latching or snapping elements in order to connect the first sawing template and the alignment instrument to each other in a force- and/or form-fitting manner. Further, a clamping connection is also conceivable.

The alignment instrument preferably has at least one abutment body with at least one contact surface for abutting against the femur or the tibia. For example, the abutment body may be configured in the form of a planar or substantially planar abutment plate. For example, it may be of substantially U-shaped configuration for placing the alignment instrument against the femur for positioning the first sawing template before placing a distal saw cut on the femur. Alternatively, two or more abutment bodies may be provided, for example two bar-shaped abutment bodies with which the alignment instrument may be positioned in a defined manner, in particular navigation-supported, on the tibia in order to fix the first sawing template on the tibia in a desired manner, e.g., in order to place the first distal tibia cut. In particular, two or more abutment bodies may be arranged so as to be moveable relative to each other in order to enable a relative position thereof on bones of different patients. In particular, an abutment body for an intramedullary orientation on the tibia may be inserted into a bore opening the medullary canal of the tibia. With the second abutment body which may be of pin-shaped configuration, the deepest point on the tibial plateau may be palpated in order to define a cutting plane at which as little bone substance on the tibia as possible is removed.

It is further advantageous if the alignment instrument comprises at least one distance changing device for varying a distance between the at least one abutment body and the at least one second connecting element. This further development enables in particular displacing or aligning a cutting plane, which is given by one of the three guidance slots on the first sawing template, in a desired manner.

It may hereby be advantageous in particular if the distance changing device is configured to displace the first sawing template in a direction perpendicular to one of the three guidance slots. This allows in particular displacing one of the three guidance slots parallel to itself in order to thus vary a cut level without influencing an orientation of the cutting plane.

It is favorable if the instrumentarium is configured to prepare the femur and the tibia and if the instrumentarium exclusively comprises two sawing templates, namely the first sawing template and the second sawing template. As already mentioned at the outset, this design enables minimizing the number of necessary sawing templates of the instrumentarium to at most two. This reduces both an expenditure in the production and in the provision and preparation of the instrumentarium.

In accordance with a further preferred embodiment of the invention, provision may be made for the first sawing template and/or the second sawing template to be configured as a disposable instrument. In particular, one or both sawing templates may be manufactured individual to a patient. In this way, a preparation, i.e. a cleaning and sterilization of the used instrumentarium, may be dispensed with.

Further, the present invention relates to a surgical instrumentarium for preparing a femur and a tibia for the implantation of a knee joint endoprosthesis, which instrumentarium comprises a first sawing template with three guidance slots for guiding a saw blade, which three guidance slots define three intersecting cutting planes, wherein the instrumentarium comprises a second sawing template, wherein the second sawing template has a fourth guidance slot for guiding a saw blade, wherein the first sawing template and the second sawing template are coupled to each other in at least one of a force- and form-fitting manner in a coupling position and are separated from each other in a separating position, wherein the three cutting planes intersect in three intersection lines, wherein the three intersection lines run parallel to each other, wherein the instrumentarium comprises an alignment instrument and wherein the alignment instrument and the first sawing template are connected to each other in at least one of a force- and form-fitting manner in an alignment position and are separated from each other in a storing position.

Depicted for example in the Figures is an instrumentarium designated as a whole with the reference numeral 10. It comprises a first sawing template 12 and a second sawing template 14. Further, the instrumentarium 10 may also comprise an alignment instrument 16.

The instrumentarium 10 is configured for preparing a femur 18 and a tibia 20 of a patient for the implantation of a knee joint endoprosthesis, not depicted in the Figures, which comprises at least one femoral component to be fixed on the femur 18 and one tibial component to be fixed on the tibia 20.

The first sawing template 12 comprises a substantially cuboidal first base body 22. Three guidance slots 24, 26, and 28 are formed thereon. Each guidance slot 24, 26, and 28 comprises two guidance slot sections which extend from lateral front faces 30 and 31 of the base body in the direction toward a symmetry plane 32 of the first sawing template 12, but not entirely up to the latter.

In order to keep a weight of the first sawing template 12 as small as possible, numerous cutouts 34 are formed, which in particular may be formed prism-like.

The guidance slots 24, 26, and 28 define cutting planes 36, 38, and 40.

The three cutting planes 36, 38, and 40 intersect in three intersection lines 42, 44, and 46, namely the cutting plane 36 with the cutting plane 40 in the intersection line 42, the cutting plane 40 with the cutting plane 38 in the intersection line 44, and the cutting plane 36 with the cutting plane 38 in the intersection line 46.

The three cutting planes 36, 38, 40 are aligned in such a way that the intersection lines 42, 44, 46 run parallel to each other.

The cutting planes 38 and 40 define between them an intersection angle 48 of 90° or substantially 90°.

The three cutting planes 36, 38, and 40 of the first sawing template 12 define jacket surfaces 50, 52, and 54 of a straight prism 56. A base surface 58 which runs transverse to the intersection lines 42, 44, and 46 has the form of a triangle 60 which is configured to be both isosceles and right-angled. Alternatively, the triangle 60 may also be configured to be equilateral.

From the upper side 62 of the first sawing template 12 projects a cuboidal coupling projection 64, the front side 66 of which defines with a front side 68 of the first base body 22 a common front side plane 70.

The coupling projection 64 forms a first coupling element 72 of a coupling device, designated as a whole with the reference numeral 74, for coupling the two sawing templates 12 and 14 in a coupling position as it is depicted for example in the FIGS. 9 and 10. The coupling device 74 further comprises a second coupling element 76 which is arranged or formed on the second sawing template 14.

The first and second coupling elements 72, 76 are in force- and/or form-fitting engagement in the coupling position and are disengaged in a separating position, as depicted for example in FIG. 11.

The second coupling element 76 is configured in the form of a coupling recess 78 which is arranged or formed on the second sawing template 14, namely in such a way that it is able to entirely accommodate the coupling projection 64.

The second sawing template 14 comprises a second base body 80 which is likewise of substantially cuboidal configuration and the front side 82 thereof is in the front side plane 70 in the coupling position.

From a lower side 84 of the second sawing template 14, which abuts on the upper side 62 in the coupling position, project two substantially cuboidal projections 86 which in the coupling position engage into a set-back portion 88 which is formed on the first base body 22 between the upper side 62 and a rear side 90. The front side 82 and the rear side 90 run approximately parallel to each other.

The rear side 90 and the a rear side 92 running parallel to the front side 82 of the second base body 80 defines in the coupling position a common rear side plane 94.

Two projections 98 project perpendicularly from an upper side 96 of the second base body 80, which projections 98 may be connected to further instruments and components of the instrumentarium 10, which are not depicted in the Figures.

The second sawing template 14 further comprises a fourth guidance slot 100 which, like the guidance slots 24, 26, and 28, serves for guiding a saw blade 192 of a surgical saw, in particular an oscillating saw.

The fourth guidance slot 100 defines a fourth cutting plane 102 which in the coupling position, as depicted for example in FIG. 10, runs parallel or substantially parallel to one of the three cutting planes 36, 38, and 40, namely to the cutting plane 36.

The projections 86 are further beveled in such a way that a guidance face 104 is formed which defines a guidance plane 106. The latter coincides in the coupling position, as schematically depicted in FIG. 10, with the cutting plane 38 and, respectively, runs slightly offset parallel thereto.

The coupling device 74 may alternatively also be configured in such a way that the first coupling element 72 is configured in the form of a coupling recess and the second coupling element 76 in the form of a coupling projection.

The coupling recess 78 on the second sawing template 14 is configured in the form of a set-back portion 108 which extends commencing from the front side 82.

Multiple fixing element receptacles 110 and 112 are arranged and formed, respectively, on the first sawing template 12. They are configured in the form of through-openings 114, 115, and 116.

The fixing element receptacles 110 serve for accommodating fixing elements 118 in the form of so-called bone pins 120 with a self-tapping tip 122 to which a bone thread section 124 connects.

A proximal end 126 of the bone pins has a substantially triangular cross section, such that it may be screwed into the femur 18 and the tibia 20, for example by an electrically driven screwdriving tool, like for example a battery screwdriver.

The through-holes 114 are each arranged in groups of three through-holes 114. They pass through the base body 22 from its front side 68 to its rear side 90.

The fixing element receptacles 112 are arranged and formed, respectively, laterally on the base body 22 so as to project.

The fixing element receptacles 110, 111, and 112 define fixing element longitudinal axes 128, 129, and 130. The fixing element longitudinal axes 128 run parallel to each other. The fixing element longitudinal axes 129 likewise run parallel to each other, but transverse to the fixing element longitudinal axes 128. The fixing element longitudinal axes 130 run inclined relative to each other and diverge facing away from the front side 82.

The second sawing template 14 likewise has multiple fixing element receptacles 132 which are arranged in groups of in each case three fixing element receptacles 132 and pass through the projections 86.

The fixing element receptacles 132 define second fixing element longitudinal axes 134 which coincide with the first fixing element longitudinal axes 130 in the coupling position. As depicted for example in FIG. 9, the bone pins 120 each pass through a fixing element receptacle 110 and a fixing element receptacle 132 oriented in alignment therewith.

The alignment instrument 16 and the first sawing template 12 are connected to each other in a force- and/or form-fitting manner in an alignment position, as it is depicted for example in FIG. 3, and are separated from each other in a storing position. FIG. 6 shows the alignment instrument 16 in the storing position without the first sawing template 12.

A connecting device 136 with a first connecting element 138 and a second connecting element 140 serves for connecting the first sawing template 12 and the alignment instrument 16. The first connecting element 138 is arranged or formed on the first sawing template 12, the second connecting element 140 on the alignment instrument 16.

The connecting elements 138 and 140 are in engagement in a force- and/or form-fitting manner in the alignment position and are disengaged in the storing position.

The first connecting element 138 is configured in the form of a connecting recess 142 with a non-round cross section, such that the connecting elements 138 and 140 may be brought into engagement with each other so as to be secured against rotation. The connecting recess 142 breaks through the first base body 22 from the front side 82 to the rear side 90.

The second connecting element 140 is formed corresponding to the first connecting element 138. It is configured in the form of a connecting projection 144 which comprises two connecting bodies 150 and 152 abutting against each other with inclined faces 146 and 148, which connecting bodies 150 and 152 may be moved toward and away from each other by way of a not-depicted mechanism which is actuatable by an adjusting screw 154, wherein a free cross section of the coupling projection 144 changes. If the connecting bodies 150 and 152 are moved toward each other, then they are laterally offset somewhat from each other, such that the cross section enlarges, whereby the coupling projection 144 may be fixed in the coupling recess 142 in a clamping manner.

Spatially separated from the second connecting element 140, the alignment instrument 16 may optionally be connected to one or more abutment bodies 156 and 158 and 160, respectively.

The abutment body 156 serves for abutting against distal end faces 162, namely condyles which in an extended joint position face in the direction toward the tibia, of the femur. Said abutment body 156 is configured substantially in the form of a U-shaped abutment plate 164. For connecting the abutment body 156 to the alignment instrument 16, a latching connecting device, which may comprise, e.g., a ball pressing piece, for coupling the alignment instrument 16 to the abutment body 156 in a force- and/or form-fitting manner.

The abutment bodies 156 and 158 are configured in the form of a probe tip 166, for example of an intramedullary rod 168. They serve for abutting the alignment instrument 16 against the tibia 20. The rod 168 is inserted into a bore 170 opening the medullary canal of the tibia 20. The probe tip 166 serves to palpate the deepest point of the tibial plateau 172.

The abutment body 156 defines a planar contact surface 174, the probe tip 166 a contact surface 176 in the form of a flattened tip. A contact surface 178 of the rod 168 is formed by the cylindrical outer surface thereof.

The alignment instrument 16 further comprises a distance changing device 180 for varying a distance 182 between the abutment body 156 and 158 or 160, respectively, on the one hand, and the second connecting element 140 on the other hand.

The distance changing device 180 is configured in particular to displace the abutment body 156 and 158 and 160, respectively, coupled to the alignment instrument 16, in parallel to a longitudinal axis 184 of the second connecting element 140. For this purpose, the distance changing device 180 has a spindle drive 186 with an adjustment knob 188 which has a scale 190 on which a surgeon may directly read an adjusted displacement path and adjust a desired displacement path, respectively.

The first sawing template 12 and/or the second sawing template 14 may in particular be configured as a disposable instrument, for example of a metal and/or a plastic. The sawing templates 12 and 14 may in particular be produced of a solid material by machining or by a shaping process like, for example, injection molding. Alternatively, the sawing templates 12 and 14 may also be formed by a generative manufacturing process like in particular 3D-printing or selective laser sintering.

As already mentioned, the instrumentarium 10 is configured to repair both the femur 18 and the tibia 20. It comprises exclusively the two sawing templates 12 and 14.

The functioning of the instrumentarium 10 is explained again briefly in the following in connection with the Figures.

First the alignment instrument 16 is connected to the first sawing template 12. For this purpose, the connecting projection 144 is inserted into the connecting recess 142 and fixed in a clamping manner by rotating the adjusting screw 154 clockwise. The alignment instrument 16 is further coupled to the abutment body 156. The unit prepared in that way of a first sawing template 12 and an alignment instrument 16 is depicted in FIG. 3.

The unit is brought with the contact surface 174 up to the end faces 162 of the femur 18. The first sawing template 12 is then fixed laterally on the femur 18 with two fixing elements 118, after a desired distance 182 between the contact surface 174 and the connecting element 140 is adjusted. This distance 182 also enables in particular an adjustment of a distance between the cutting plane 36 and the contact surface 174.

If the first sawing template 12 is positioned in a desired manner relative to the contact surface 174, then it is fixed laterally on the femur 18 with two fixing elements 118. A distal cut on the femur 18 is performed with an oscillating saw which comprises a saw blade 192. For this purpose, the saw blade 192 is guided in the guidance slot 24 and successively inserted into the two sections thereof, respectively. The first planar distal femoral face 194 may be prepared in this way.

In a next step, the first sawing template 12 is removed from the femur 18 and now placed with its rear side 90 against the prepared femoral face 194. The first sawing template is fixed on the femur 18 with two fixing elements 118 which are inserted through the fixing element receptacles 112. An alignment of the first sawing template 12 may take place before its fixation, in particular with the support of a navigation system.

Then the second sawing template 14 is coupled to the first sawing template 12 in the manner described above. The second sawing template 14 is likewise fixed on the femur 18 with two further fixing elements 118. Said two fixing elements 118 also pass through the first sawing template 12, as may be seen in FIG. 9.

Now four further saw cuts may be performed on the femur 18 with the saw, which cuts are guided by the total of four guidance slots 24, 26, 28, and 100. In this way, four further planar femoral faces, not illustrated in more detail in the Figures, may be prepared in addition to the femoral face 194. The sawing templates 12 and 14 coupled to each other thus form a 4-in-1 sawing template.

After the preparation of the femur 18, the sawing templates 12 and 14 are again removed.

For the preparation of the tibia 20, the abutment body 156 is removed from the alignment instrument 16. Now the abutment bodies 158 and 160 are connected to the alignment instrument 16. The alignment instrument 16 in turn is connected to the first sawing template 12 in the described manner.

The rod 168 is inserted into the opened intramedullary canal of the tibia 20 and the deepest point of the tibial face 172 is palpated with the contact surface 176 of the probe tip 166. In a normal position of the distance changing device 180, the guidance slot 24 runs at the level of the contact surface 176. By rotating the adjustment knob 188, a position of the first sawing template 12 may be varied in order to resect more or less from the tibia 20.

When the position of the first sawing template 12 is adjusted in a desired manner, then the same is fixed again on the tibia 20 with two or more fixing elements 118. The guidance slot 24 serves in turn for guiding the saw blade 192 in order to form a planar tibial face which faces in the direction of the femur 18 when the leg is outstretched, i.e. in an extended position.

The described instrumentarium 10 manages with a minimal number of sawing templates, namely with exactly two. Said instrumentarium 10 may be provided optionally as a reusable or disposable instrumentarium.

REFERENCE NUMERAL LIST 10 instrumentarium
12 first sawing template
14 second sawing template
16 alignment instrument
18 femur
20 tibia
22 first base body
24 guidance slot
26 guidance slot
28 guidance slot
30 front face
31 front face
32 symmetry plane
34 cutouts
36 cutting plane
38 cutting plane
40 cutting plane
42 intersection line
44 intersection line
46 intersection line
48 intersection angle
50 jacket surface
52 jacket surface
54 jacket surface
56 prism
58 base surface
60 triangle
62 upper side
64 coupling projection
66 front side
68 front side
70 front side plane
72 first coupling element
74 coupling device
76 second coupling element
78 coupling recess
80 second base body
82 front side
84 lower side 86 projections
88 set-back portion
90 rear side
92 rear side
94 rear side plane
96 side
98 projections
100 fourth guidance slot
102 fourth cutting plane
104 guidance face
106 guidance plane
108 set-back portion
110 fixing element receptacle
111 fixing element receptacle
112 fixing element receptacle
114 through-opening
115 through-opening
116 through-opening
118 fixing element
120 bone pin
122 tip
124 bone thread section
126 end
128 fixing element longitudinal axis
129 fixing element longitudinal axis
130 fixing element longitudinal axis
132 fixing element receptacle
134 fixing element longitudinal axis
136 connecting device
138 first connecting element
140 second connecting element
142 connecting recess
144 connecting projection
146 inclined face
148 inclined face
150 connecting body
152 connecting body
154 adjusting screw
156 abutment body
158 abutment body
160 abutment body
162 end face
164 abutment plate
166 probe tip
168 rod
170 bore
172 tibial plateau
174 contact surface
176 contact surface
178 contact surface
180 distance changing device
182 distance
184 longitudinal axis
186 spindle drive
188 adjustment knob
190 scale
192 saw blade
194 femoral face

What is claimed is:

1. Surgical instrumentarium for preparing a femur and a tibia for the implantation of a knee joint endoprosthesis, consisting of:
a first sawing template with three guidance slots for guiding a saw blade for preparing respective first, second and third planar surfaces on the femur, which three guidance slots define three intersecting cutting planes,
a second sawing template, wherein the second sawing template has a fourth guidance slot for guiding a saw blade for preparing a respective fourth planar surface on the femur,
the first sawing template and the second sawing template being coupled to each other in at least one of a force- and form-fitting manner in a coupling position and are separated from each other in a separating position,
wherein:
the three cutting planes intersect in three intersection lines,
the three intersection lines run parallel to each other,
the first sawing template and the second sawing template are adapted for making femoral saw cuts on the femur and the first sawing template is also adapted for making a tibial saw cut on the tibia such that all saw cuts on the femur and the tibia are made with only the two sawing templates comprising the first sawing template and the second sawing template,
the instrumentarium is configured for the preparation of the femur and the tibia,
the first sawing template has a first front side,
the second sawing template has a second front side,
the first front side and the second front side define a common front side plane in the coupling position,
all of the four guidance slots are accessible from the first and second front sides in the coupling position, and
the fourth guidance slot in the coupling position runs parallel or substantially parallel to one of the three guidance slots of the first sawing template.

2. Surgical instrumentarium in accordance with claim 1, wherein:
at least one first coupling element is arranged or formed on the first sawing template,
at least one second coupling element is arranged or formed on the second sawing template, and
the at least one first coupling element and the at least one second coupling element are in engagement in the coupling position and are disengaged in the separating position.

3. Surgical instrumentarium in accordance with claim 2, wherein the at least one first coupling element is configured in the form of a coupling projection or a coupling recess, and wherein the at least one second coupling element is formed corresponding to the at least one first coupling element.

4. Surgical instrumentarium in accordance with claim 3, wherein the coupling recess forming the at least one second coupling element is configured in the form of at least one set-back portion on the first or second sawing template.

5. Surgical instrumentarium in accordance with claim 1, wherein the first sawing template comprises a first base body on which the three guidance slots are formed.

6. Surgical instrumentarium in accordance with claim 1, wherein the second sawing template comprises a second base body on which the fourth guidance slot is formed.

7. Surgical instrumentarium in accordance with claim 1, wherein the first sawing template has at least one first fixing element receptacle for at least one first fixing element for selectively fixing the first sawing template on the femur or on the tibia.

8. Surgical instrumentarium in accordance with claim 7, wherein:
the second sawing template has at least one second fixing element receptacle for at least one fixing element for fixing the second sawing template on the femur;
the at least one first fixing element receptacle defines a first fixing element longitudinal axis, the at least one second fixing element receptacle defines a second fixing element longitudinal axis, and the first fixing element longitudinal axis of the at least one first fixing element receptacle and the second fixing element longitudinal axis of the at least one second fixing element receptacle coincide in the coupling position.

9. Surgical instrumentarium in accordance with claim 8, wherein: the first sawing template is connectable to an alignment instrument in at least one of a force- and form-fitting manner in an alignment position and the first sawing template and the alignment instrument are separated from each other in a storing position.

10. Surgical instrumentarium in accordance with claim 9, wherein at least one of:
a) the first sawing template comprises at least one first connecting element, at least one second connecting element is arranged or formed on the alignment instrument, and the at least one first connecting element and the at least one second connecting element are in engagement in the alignment position and are disengaged in the storing position, and
b) the first sawing template comprises at least one first connecting element, at least one second connecting element is arranged or formed on the alignment instrument, the at least one first connecting element and the at least one second connecting element are in engagement in the alignment position and are disengaged in the storing position, the at least one first connecting element is configured in the form of a connecting projection or a connecting recess, and the at least one second connecting element is formed corresponding to the at least one first connecting element, and
c) the alignment instrument has at least one abutment body with at least one contact surface for abutting against the femur or the tibia, and
d) the alignment instrument has at least one abutment body with at least one contact surface for abutting against the femur or the tibia, wherein the alignment instrument comprises at least one distance changing device for varying a distance between the at least one abutment body and the at least one second connecting element.

11. Surgical instrumentarium in accordance with claim 7, wherein at least one of:
a) the first sawing template comprises a first base body on which the three guidance slots are formed and the at least one first fixing element receptacle is arranged or formed projecting over the first base body, and
b) at least two first fixing element receptacles are provided and wherein the first fixing element longitudinal axes thereof are aligned parallel or substantially parallel or inclined relative to each other.

12. Surgical instrumentarium in accordance with claim 1, wherein the second sawing template has at least one second fixing element receptacle for at least one fixing element for fixing the second sawing template on the femur.

13. Surgical instrumentarium in accordance with claim 12, wherein at least two second fixing element receptacles are provided which define second fixing element longitudinal axes and wherein the second fixing element longitudinal axes are aligned parallel or substantially parallel or inclined relative to each other.

14. Surgical instrumentarium in accordance with claim 1, wherein at least one of:
a) two of the three cutting planes intersect at a right angle or substantially at a right angle, and
b) the three cutting planes of the first sawing template define jacket surfaces of a straight prism which has a base surface in the form of a triangle.

15. Surgical instrumentarium in accordance with claim 1, wherein at least one of the first sawing template and the second sawing template are configured as a disposable instrument.

16. Surgical instrumentarium in accordance with claim 1, wherein the first sawing template and the second sawing template are adapted for making at least one of the femoral saw cuts on the femur when in the coupling position.

17. Surgical instrumentarium in accordance with claim 1, wherein the first sawing template and the second sawing template are each of monolithic design.

18. Surgical instrumentarium in accordance with claim 1, wherein any two of the three guidance slots of the first sawing template intersect each other.

19. Surgical instrumentarium in accordance with claim 1, wherein the first sawing template comprises a first base body on which the three guidance slots are formed, and wherein two of the three cutting planes intersect each other within the first base body.

20. Surgical instrumentarium for preparing a femur and a tibia for the implantation of a knee joint endoprosthesis, consisting of:
a first sawing template with three guidance slots for guiding a saw blade for preparing respective first, second and third planar surfaces on the femur, which three guidance slots define three intersecting cutting planes,
a second sawing template, wherein the second sawing template has a fourth guidance slot for guiding a saw blade for preparing a respective fourth planar surface on the femur,
the first sawing template and the second sawing template being coupled to each other in at least one of a force- and form-fitting manner in a coupling position and are separated from each other in a separating position,
wherein:
the three cutting planes intersect in three intersection lines,
the three intersection lines run parallel to each other,
the first sawing template and the second sawing template are adapted for making femoral saw cuts on the femur and the first sawing template is also adapted for making a tibial saw cut on the tibia such that all saw cuts on the femur and the tibia are made with only the two sawing templates comprising the first sawing template and the second sawing template,
the instrumentarium is configured for the preparation of the femur and the tibia,
the first sawing template has a first front side,
the second sawing template has a second front side,
the first front side and the second front side define a common front side plane in the coupling position,
all of the four guidance slots are accessible from the first and second front sides in the coupling position, and
the second sawing template has a guidance face, wherein the guidance face defines a guidance plane, and wherein the guidance plane in the coupling position is defined by one of the three cutting planes.

21. Surgical instrumentarium in accordance with claim 20, wherein the fourth guidance slot in the coupling position runs parallel or substantially parallel to one of the three guidance slots of the first sawing template.

22. Surgical instrumentarium for preparing a femur and a tibia for the implantation of a knee joint endoprosthesis, consisting of:
- a first sawing template with three guidance slots for guiding a saw blade for preparing respective first, second and third planar surfaces on the femur, which three guidance slots define three intersecting cutting planes,
- a second sawing template, wherein the second sawing template has a fourth guidance slot for guiding a saw blade for preparing a respective fourth planar surface on the femur,
- the first sawing template and the second sawing template being coupled to each other in at least one of a force- and form-fitting manner in a coupling position and are separated from each other in a separating position, wherein:
- the three cutting planes intersect in three intersection lines,
- the three intersection lines run parallel to each other,
- the first sawing template and the second sawing template are adapted for making femoral saw cuts on the femur and the first sawing template is also adapted for making a tibial saw cut on the tibia such that all saw cuts on the femur and the tibia are made with only the two sawing templates comprising the first sawing template and the second sawing template,
- the instrumentarium is configured for the preparation of the femur and the tibia,
- the first sawing template has a first front side,
- the second sawing template has a second front side,
- the first front side and the second front side define a common front side plane in the coupling position,
- all of the four guidance slots are accessible from the first and second front sides in the coupling position, and
- the fourth guidance slot defines a fourth cutting plane and wherein the fourth cutting plane in the coupling position runs parallel or substantially parallel to one of the three cutting planes of the first sawing template.

23. Surgical instrumentarium for preparing a femur and a tibia for the implantation of a knee joint endoprosthesis, consisting of:
- a first sawing template with three guidance slots for guiding a saw blade for preparing respective first, second and third planar surfaces on the femur, which three guidance slots define three intersecting cutting planes,
- a second sawing template, wherein the second sawing template has a fourth guidance slot for guiding a saw blade for preparing a respective fourth planar surface on the femur, and
- an alignment instrument,
- the first sawing template and the second sawing template being coupled to each other in at least one of a force- and form-fitting manner in a coupling position and are separated from each other in a separating position, wherein:
- the three cutting planes intersect in three intersection lines,
- the three intersection lines run parallel to each other,
- the alignment instrument and the first sawing template are connected to each other in at least one of a force- and form-fitting manner in an alignment position and are separated from each other in a storing position,
- the first sawing template and the second sawing template are adapted for making femoral saw cuts on the femur and the first sawing template is also adapted for making a tibial saw cut on the tibia such that all saw cuts on the femur and the tibia are made with only the two sawing templates comprising the first sawing template and the second sawing template,
- the instrumentarium is configured for the preparation of the femur and the tibia,
- the first sawing template has a first front side,
- the second sawing template has a second front side,
- the first front side and the second front side define a common front side plane in the coupling position,
- all of the four guidance slots are accessible from the first and second front sides in the coupling position, and
- the fourth guidance slot defines a fourth cutting plane and wherein the fourth cutting plane in the coupling position runs parallel or substantially parallel to one of the three cutting planes of the first sawing template.

* * * * *